United States Patent [19]

Scheibengraber

[11] Patent Number: 4,538,289
[45] Date of Patent: Aug. 27, 1985

[54] REFLECTIVE ALIGNMENT LIGHT FOR COMPUTERIZED TOMOGRAPHY

[75] Inventor: Karl J. Scheibengraber, Milwaukee, Wis.

[73] Assignee: General Electric Company, Milwaukee, Wis.

[21] Appl. No.: 335,024

[22] Filed: Dec. 28, 1981

[51] Int. Cl.³ .............................................. G03B 41/16
[52] U.S. Cl. ....................................... 378/20; 378/206
[58] Field of Search .................. 378/20, 206; 356/138, 356/247, 248

[56] References Cited

U.S. PATENT DOCUMENTS

| 3,854,820 | 12/1974 | Hansen | 356/138 |
| 4,117,337 | 9/1978 | Staats | 250/445 |
| 4,296,329 | 10/1981 | Mirabella | 378/206 |

OTHER PUBLICATIONS

Article Entitled "Electro-Mechanical Mirror Scanning" from The Optical Industry and Systems Purchasing Directory, 1980.

*Primary Examiner*—Craig E. Church
*Attorney, Agent, or Firm*—Douglas E. Stoner

[57] ABSTRACT

The conventional cylindrical lens of a laser alignment device is replaced with a non-planar reflective device for spreading the collimated laser beam into a fan-shaped linear pattern for patient alignment use. In one form, a mirror-coated cylindrical rod is used to generate axial alignment lines, and in another form, a mirror-coated cone is used to generate the coronal alignment lines.

2 Claims, 8 Drawing Figures

REFLECTIVE CONE (CONICAL MIRROR)

REFLECTIVE ALIGNMENT LIGHT FOR COMPUTERIZED TOMOGRAPHY

This invention relates generally to patient-alignment devices and, more particularly, to a device for properly positioning a patient on the table of a computerized tomography system.

Conventional computerized tomography systems include an upright gantry portion having a central opening formed therein and an adjacent, generally horizontally-disposed table on which the patient reclines for the longitudinal advancement into the central opening to facilitate the scanning process. Located within the gantry, in diametric opposition to a point at the center of the central opening referred to as the isocenter, are a radiation source and a detector. In order to effect a scan, at least one, and preferably both, of the source and detector are rotated about the patient when in the advanced position to thereby direct radiation from the source, through the patient and into the detector. As the rotation of the scan proceeds, a number of views are presented to the detector, and resultant signals are produced which are representative of the energy attenuation at each one of the views. The signals are then digitized and accumulated in a processor where certain algorithms are performed for the subsequent reconstruction of the image and display on a CRT monitor. The image is a cross-sectional view of the patient within the scan plane, i.e., generally perpendicular to the longitudinal axis of the central opening along which the patient is advanced. It is, of course, common practice to obtain oblique views through the patient by a tilting of the patient or of the gantry itself.

The thickness of the image slice is determined by the thickness (in the longitudinal direction) of the radiation fan beam and is on the order of 1 to 10 mm. Even though, during a normal diagnostic procedure, a number of adjacent scans are made, it is still very important to know the precise location of the patient with respect to the scan plane. This is important for two reasons. First, it is desirable to minimize the amount of radiation to which the patient is exposed, and, therefore, it is desirable to minimize the number of scans that are made. Second, and more important, is the desirability of scanning the precise region of interest within the patient's body. In order to accomplish this it is necessary to be able to precisely position the patient with respect to the scan plane. Similarly, in addition to this requirement for proper longitudinal or axial placement, it is also extremely desirable to maintain proper lateral and height placement of the patient with respect to the isocenter.

A common approach for obtaining patient alignment is to provide within the gantry a number of light sources which project in the direction of the isocenter such that a stationary light pattern appears on the patient and thereby provides an indication of whether or not the patient is in the proper position. The source of light used in this arrangement is often a laser beam which is diverged in a linear form by a cylindrical lens or the like.

A problem exists with the above approach in that the isocenter is well into the central opening such that, because of the restricted viewing angle, it is difficult to precisely apply the light patterns in order to obtain precise positioning. Accordingly, a known solution is to provide alignment lights in a more accessible position in advance of the isocenter such that an unrestricted view may be obtained. One such apparatus is shown and described in U.S. Pat. No. 4,117,337, assigned to the assignee of the present invention. This arrangement is commonly referred to as an "external" alignment device as compared with the so-called "internal" alignment device which is in axial alignment with the isocenter.

Another type of external alignment light is that shown in U.S. application Ser. No. 314,170, filed on Oct. 23, 1981, and assigned to the assignee of the present invention. Here the external alignment lights are positioned within the gantry but still well in advance of the internal alignment lights in the scan plane. It should be mentioned that a preferred arrangement is to have both internal and external alignment lights for maximum flexibility in applying the scanning procedures.

In the prior art approach of using cylindrical lenses, a laser is positioned so as to direct its beam in the general direction of the reclining patient. A glass rod is then placed in the path of the beam, in perpendicular relation thereto, such that the substantially point source beam is spread into a sector form which appears in linear form at the area to be occupied by the patient. Such a refractive approach of spreading the laser beam into a sector pattern necessarily involves the use of a glass lens which is susceptible to breakage and gradual misalignment. Should a lens break, it will, of course, then cause the operator to be inconvenienced by the requirement for placement. More important, it will result in an unrefracted or "bare" laser beam projecting into the patient area where it could enter the patient's eyes and cause retinal damage.

Other disadvantages to the use of cylindrical lenses include the inherent intensity losses that occur at the air-glass-air interfaces of the lenses. Generally, it may be said that at each one of these interfaces four percent of the light intensity will be lost so that in the typical cylindrical lens a total of eight percent of the laser light intensity is lost.

Another problem with the cylindrical lens is that the beam may come to a focus within the confines of the lens which results in a distorted line.

Still another problem is that with the cylindrical lens, in order to obtain a line of sufficient length, it is necessary to use a lens of relatively small diameter (e.g., 1 mm.), which in turn is difficult to handle.

It is therefore an object of the present invention to provide an improved patient-alignment system for a computerized tomography system.

Another object of the present invention is the provision in a patient-alignment system for the elimination of glass lenses which could break or dislodge and thus allow the direct beam to impinge into the patient area.

Yet another object of the present invention is to provide a patient alignment apparatus which is not susceptible to the projection of a "bare" laser beam in the vicinity of a patient.

Still another object of the present invention is the provision in a laser-based patient-alignment system for reducing light intensity losses and internal focussing problems.

These objects and other features and advantages become readily apparent upon reference to the following description when taken in conjunction with the appended drawings.

SUMMARY OF THE INVENTION

Briefly, in one aspect of the invention, the refractive element of the conventional apparatus is replaced with a reflective element and the positions of both the laser source and the reflector are established so as to obtain a linear light pattern in the desired location in the vicinity of the patient. A laser beam is projected in a direction substantially perpendicular to the direction which the linear pattern must travel in order to reach the staged patient. A non-planar reflecting medium is placed in the path of the laser beam in such a position as to reflect and diverge the beam into an expanding line of light. This line is projected toward the CT table as a reference light with respect to which the patient can be selectively positioned. The reference position corresponds to a scan plane to which the patient is subsequently advanced.

In one form, the reflective medium is comprised of a mirror-coated cylindrical rod fabricated of metal, glass, or plastic. The laser beam is directed to the rod, in a perpendicular relationship thereto, to thereby result in a reflected linear form which occupies a sector of a plane that includes the undiverged laser beam. The size of the rod can be substantially larger than that of a cylindrical lens that performs the same function. For example, a 4 mm. cylindrical mirror can replace a 2 mm. cylindrical lens to obtain a line of the same length. Ease of handling is therefore substantially improved.

By another aspect of the invention, the reflective medium comprises a mirror-coated cone disposed coaxially with the laser beam. The resulting projected fan then occupies a sector in a plane which is perpendicular to the undiverged laser beam.

In the drawings as hereinafter described, a preferred embodiment and modified embodiments are depicted; however various other modifications and alternate constructions can be made thereto without departing from the true spirit and scope of the invention.

DESCRIPTION OF THE PREFERRED EMBODIMENT

Figure 1:
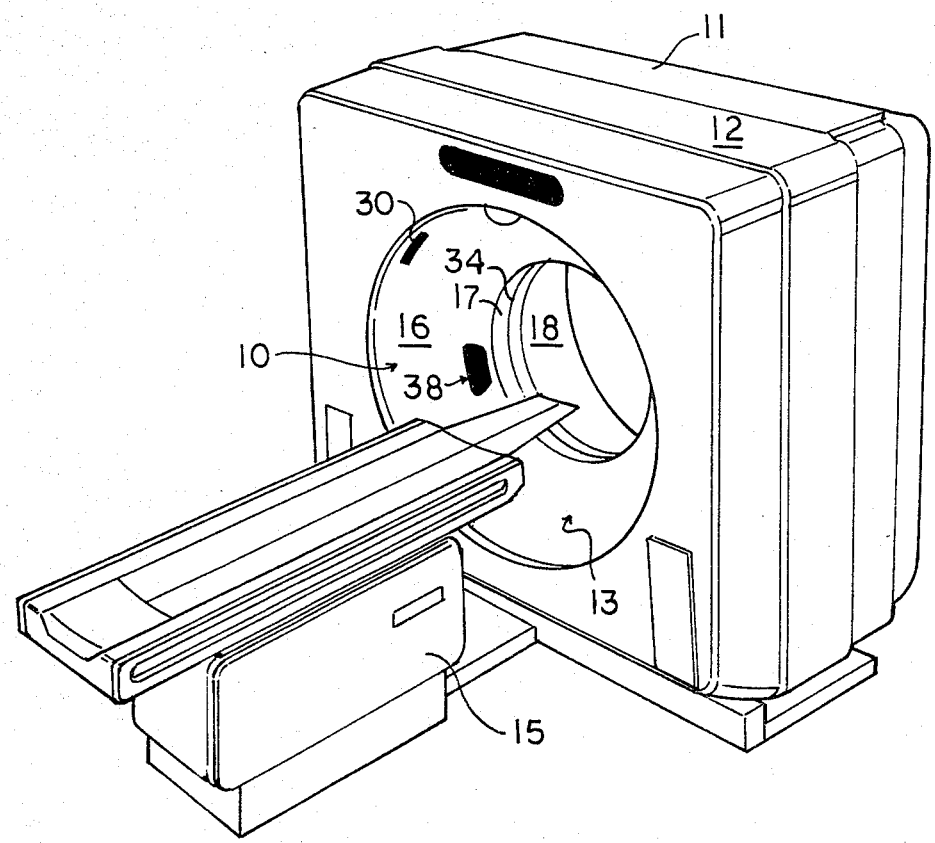
FIG. 1 is a perspective view of a computerized tomography system with which the present invention is applicable.
Figure 2:
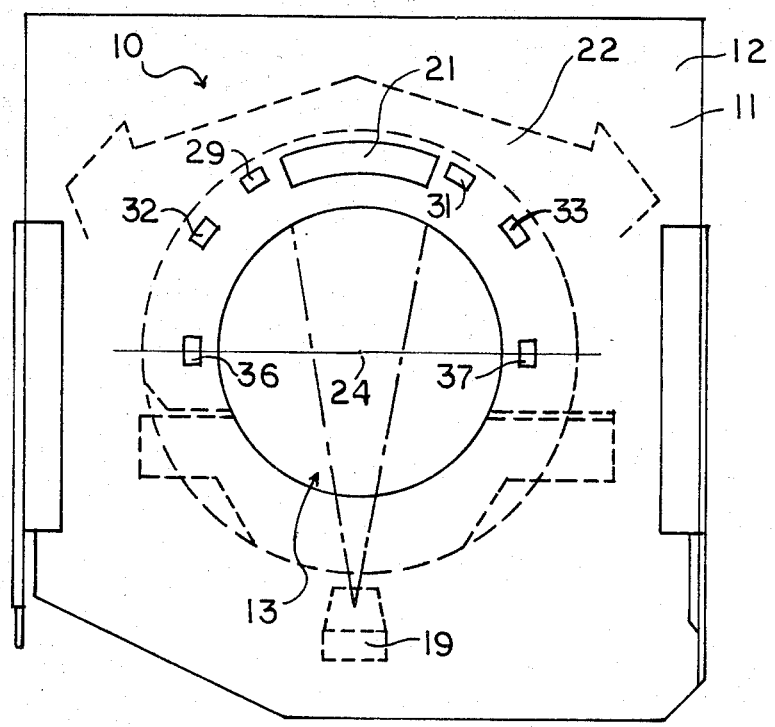
FIG. 2 is a front view of the gantry portion thereof showing the locations of the alignment devices of the present invention.
Figure 3:
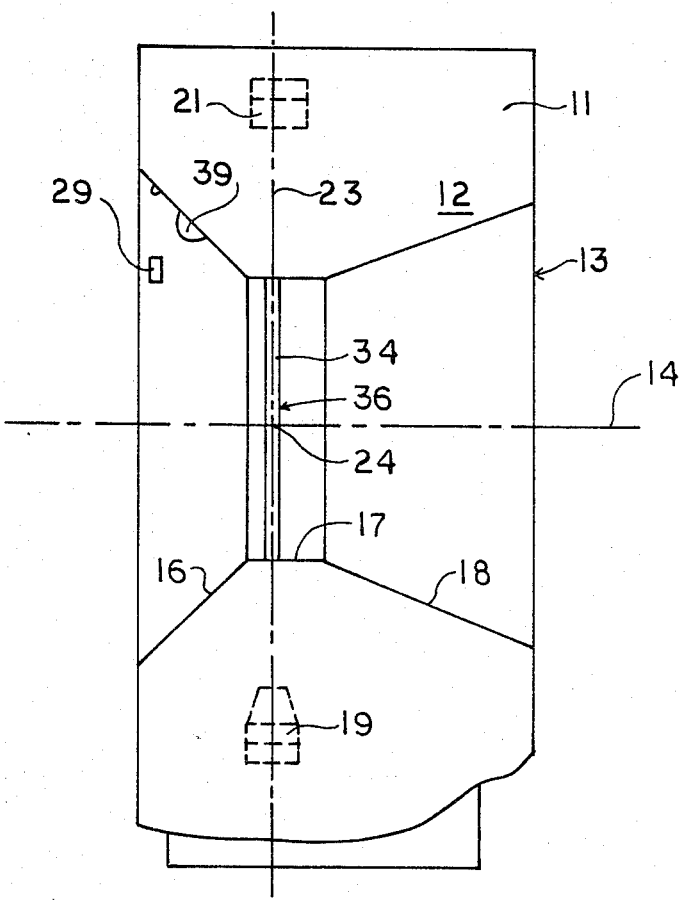
FIG. 3 is a side view of a computerized tomography system with the alignment devices of the present invention.

Referring now to the drawings, wherein like numerals correspond to like elements throughout, reference is initially made to FIGS. 1, 2, and 3, the invention is shown generally at 10 as installed in a computerized tomography system comprising a gantry 11 and a patient-support table 15. The gantry 11 includes a cover or shroud 12 which is generally rectangular in form at its outer boundaries and which has a central opening or tunnel 13 formed along a longitudinal axis 14. The shroud tunnel 13 is made up of converging portion 16, cylindrical portion 17, and the diverging portion 18, with the shape being determined by the need for easily positioning and observing the patient within the tunnel during an examination. Housed within the gantry shroud 12 are an X-ray source 19 and a detector 21, both of which are mounted on a detector plate 22 on opposite sides of the tunnel, such that their common plane, which will hereinafter be referred to as the scanning plane 23, intersects the tunnel longitudinal axis 14 at a point commonly referred to as the isocenter 24. The X-ray source 19 is adapted to emit a thin fan-shaped beam of X-rays along the scanning plane 23, through the isocenter 24 and to the detector 21.

The patient table 15 is disposed in front of the gantry 11 and includes a translatable cradle which is adapted to support the patient in a generally horizontal position. A drive means is provided within the table to translate the cradle and patient along the longitudinal axis to a position in the scan plane 23.

During the X-ray examination, the patient 27 is exposed to the fan beam of radiation from the source 19, and the detector 21 is operable to measure the attenuation of X-ray energy by the patient. The detector 21 is typically made up of a plurality of cells with each cell being capable of making its own independent measurement related to its sector of the fan beam within a scan plane. The responsive signals from all of the detector cells, at an instant of patient exposure, constitutes a view of the patient through the scan line.

During an examination scan, the source 19 and detector 21 are rotated by way of the detector plate 22 around the patient to obtain a number of views. The data from all of the views is then combined by appropriate algorithms so as to reconstruct an image of the slice through the patient at the scan plane in a well-known manner.

It should be mentioned that, while the present invention is being described in terms of use with a so-called third generation scanner, wherein both the source and detector are rotated about the patient, it could just as well be used with other types of scanners such as, for example, a so-called fourth generation scanner wherein either, but not both, of the source or detector is rotated about the patient.

In order to facilitate scans in oblique planes, provision is made to tilt the gantry 11 within its base to either side of the vertical plane such that the scanning plane 23 makes an oblique angle with the longitudinal axis 14. A typical mechanism for effecting this tilting function is shown and described in U.S. Pat. No. 4,093,860, assigned to the assignee of the present invention.

It is known that to successfully scan the anatomy of interest, the patient must be precisely positioned in relation to the scan plane 23. This may be done when the patient is in the advanced position within the scan plane 23. One way in which this is accomplished is by way of so-called internal alignment lights located in the gantry and used for projecting a light pattern on the patient to indicate the position of the patient with respect to the scanning plane. Also, it is well known that the use of such internal alignment lights can often be difficult in practice because of the relative inaccessibility to the operator of the patient once the patient is in the advanced position.

An alternative or complementary approach is to selectively align the patient with respect to an external reference indicator located in a more accessible position outside of the tunnel as shown by solid lines in FIG. 3, and then advance to the patient cradle 26 and supported patient 27 a distance equal to the longitudinal distance between the reference indicator and the scanning plane. In the present invention, the reference indicator is provided by so-called external alignment lights mounted within the gantry but located well forward of the scanning plane, such that the operator can easily visualize the projection of the light patterns on the patient when in the staged position. A description of both the internal and external alignment lights will now be given.

Figure 4:
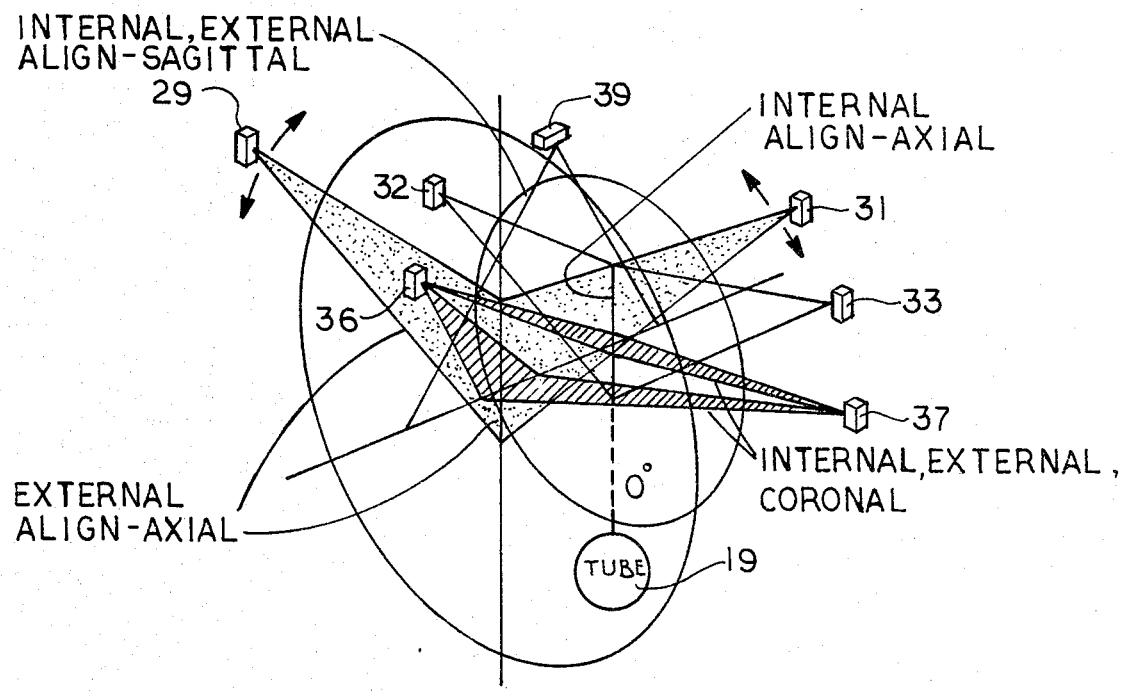
FIG. 4 is a schematic illustration of the alignment lights in a typical computerized tomography system.

The axial alignment lights are shown in FIGS. 2, 3, and 4 and comprise the external axial alignment lights 29 and 31 and the internal axial alignment lights 32 and 33. The external axial alignment lights 29 and 31 project complementary fan-shaped beams from positions inside the gantry toward the patient by way of cutouts or windows as shown at 30. The internal lights 32 and 33 are located in the scan plane and project their complementary beams within that scan plane through a transparent hoop 34 made from a material such as Mylar. The function of the axial alignment lights is, of course, to facilitate the proper axial placement of the patient along the longitudinal axis or, said in another way, to assist in the selection of the slice that is to be imaged.

To aid in the selection of the proper height to which the patient is placed, the coronal alignment lights 36 and 37 are located in the horizontal plane of the longitudinal axis 14 so as to project a horizontal line onto each side of the patient. As shown in FIGS. 1 and 4, a single pair of lights serves to provide both the internal and external coronal patterns with the light for the external being projected through a window 38 having the form of a truncated sector, and the light beam for the internal coronal being projected through the Mylar hoop 34. It should be mentioned that, whereas the axial and sagittal alignment lines tilt with the gantry, the coronal lines must remain in a horizontal disposition and therefore it is necessary to provide a means which will maintain this horizontal disposition regardless of gantry tilt. This feature will be more fully discussed hereinafter.

The sagittal alignment light 39 is adapted to project a fan beam downwardly on the patient as shown in FIG. 4 and serves as both the external and internal reference means.

The location and the function of the various alignment lights have been described. The internal and external axial alignment lights will now be discussed in more detail. In particular, the manner in which the specific patterns are generated will be described in terms of the reflective concept of the present invention. For ease of description, the components and installation will be described in terms of the external axial alignment light 29; however, it will be understood that the same features and advantages apply as well to the other axial alignment lights 31, 32, and 33.

Mounted on the rotatable detector plate 22 is a power source 41 and a laser 42, the power source being connected to the laser by way of a high voltage co-axial cable, not shown. At the emission end of the laser 42 is mounted a bracket 43 for holding a mirror-coated rod 44 in the path of the projected laser beam. The rod or cylindrical reflector can be fabricated from a reflective material such as, for example, glass stirring rod or stainless steel rod.

Figure 6:
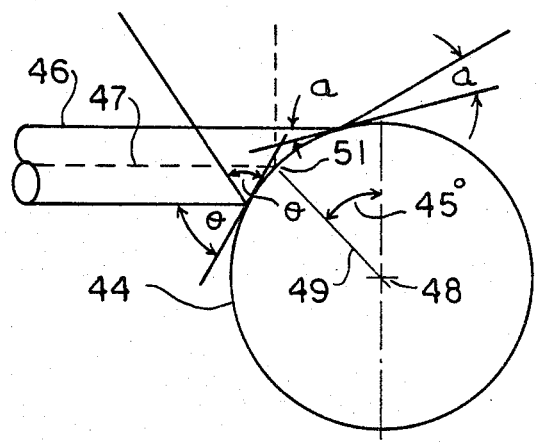
FIG. 6 is a schematic illustration of how a scan line is generated by the reflection of a laser beam from the reflective rod of the FIG. 4 appapatus.

A description of the manner in which the laser beam 46 interacts with the cylindrical reflector 44 is shown in FIG. 6. It will be seen that the two are positioned such that the central axis 47 of the laser beam 46 is normal to but offset from the longitudinal axis 48 of the rod 44. For reasons that will be apparent, the amount of offset is usually such that the central axis 47 of the laser beam intersects with the end of the radial line 49 which is 45° from the direction in which the desired pattern is to be projected. It is at this intersection point that the light is reflected at a 90° angle from the beam central axis 47. On either side of that point, the light will be reflected either at a greater or a lesser angle than 90° so as to thereby spread the laser beam out as shown to project a straight line. The length of the projected line will be determined by the angles of incidence, $\theta$ and $\alpha$, of the beam boundaries as shown. Of course, the relative sizes of the laser beam and the reflective rod can be varied to obtain the desired effect. A typical installation comprises a laser having a beam diameter of 0.7 (mm. at $1/e^2$) and a rod with a diameter of 4 mm.

It will, of course, be understood that the reflective rod approach as described above could be used for the sagittal light by projecting a laser in the generally longitudinal direction and placing in its path a cylindrical rod with its axis aligned in the generally transverse direction so as to direct the light fan down onto the patient.

Figure 5:
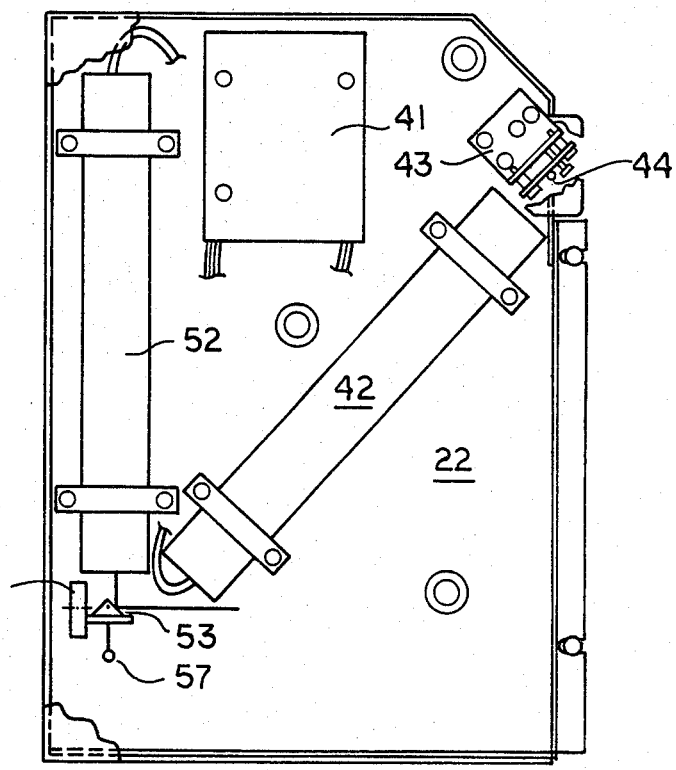
FIG. 5 is a front view of the preferred embodiment of the invention.
Figure 7:
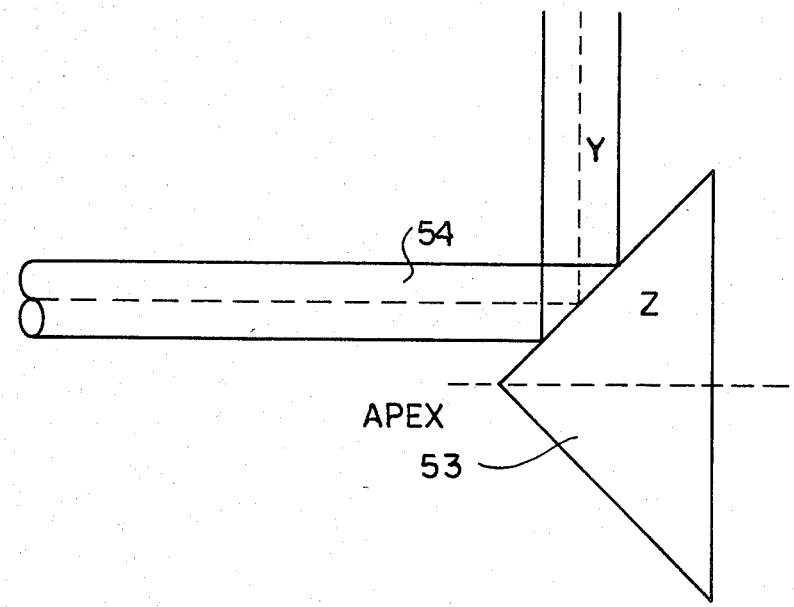
FIGS. 7A and 7B are schematic illustrations of how a scan line is generated with the use of a modified embodiment of the present invention.
Figure 7:
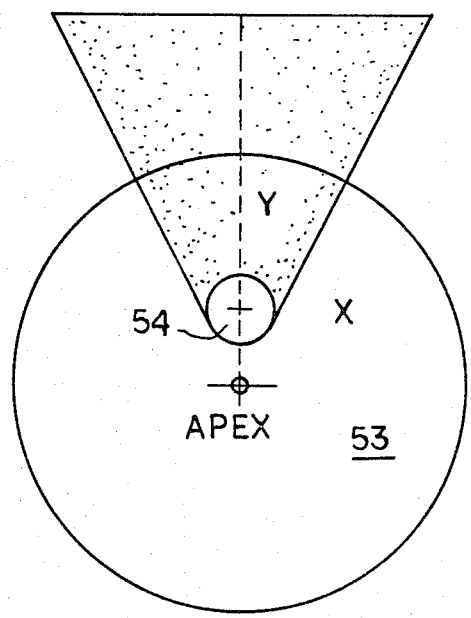

In addition to the cylindrical rod approach, there are other reflector forms which may be used. A prime example is a cone-shaped reflector which is particularly useful for generating the coronal alignment line. As shown in FIG. 5, a laser 52 is mounted to the detector plate 22 such that its light projects in the downward direction as shown. Situated in the path of the laser beam is a right circular cone 53 having a highly reflective surface. The cone 53 is positioned such that the reflected light is fanned out to project a horizontal beam at the height of the longitudinal axis 14. These geometric relationships between the laser beam 54 and the cone 53 are shown in FIGS. 7a and 7b. It will be recognized that the length of the projected line will be dependent on the diameter of the laser beam 54 and on the location of the point at which it strikes the cone 53. The closer it strikes to the apex, the longer will be the projected reflection at a given distance.

In order to accommodate a tilting of the gantry without an associated tilting of the coronal reference line, it is necessary to isolate the cone 53 from the effects of tilt. This is done by pivotally mounting the cone 53 on a shaft 56 and including a depending weight or pendulum 57 so as to maintain its vertical disposition regardless of the gantry tilt. The shaft 56 is located on the axis of gantry rotation such that the position of the cone 53 remains constant regardless of gantry tilt.

While the applicant has described a preferred embodiment of two forms of the inventive concept, it should be clear to those skilled in the art that changes could be made in the embodiments described herein without departing from the broad aspects of the invention. It is intended, therefore, that the appended claims cover all such modifications which fall within the broad aspects of the applicant's invention.

I claim:

1. In a computerized tomography system having a gantry with a central opening and into which a patient can be placed for scanning, an alignment device for positioning a patient with respect to the central opening comprising: a source for projecting a beam of collimated light; and a reflective cylindrical rod disposed in such a position as to reflect said beam of collimated light in a diverging linear pattern.

2. A patient-alignment apparatus for positioning a staged patient for subsequent longitudinal advancement into the cylindrical gantry opening of an X-ray scanner having an X-ray source and detector means for scanning the patient to produce a tomographic image in the plane of the scan comprising: a light source for projecting a light beam in a direction away from the patient; non-planar reflecting means attached to a supporting element and disposed in such a position as to reflect said beam as a reference line on the staged patient; and mounting and pendulum means for maintaining said non-planar reflecting means in a fixed position with respect to said light beam irrespective of the rotation of the supporting element to which it is mounted.

* * * * *